(12) United States Patent
Molloi

(10) Patent No.: US 10,898,150 B2
(45) Date of Patent: Jan. 26, 2021

(54) VESSEL CROSS-SECTIONAL AREA MEASUREMENT USING CT ANGIOGRAPHY

(71) Applicant: THE REGENTS OF THE UNIVERSITY OF CALIFORNIA, Oakland, CA (US)

(72) Inventor: Sabee Molloi, Irvine, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 485 days.

(21) Appl. No.: 15/832,623

(22) Filed: Dec. 5, 2017

(65) Prior Publication Data

US 2018/0153494 A1 Jun. 7, 2018

Related U.S. Application Data

(60) Provisional application No. 62/429,971, filed on Dec. 5, 2016.

(51) Int. Cl.
*A61B 6/00* (2006.01)
*A61B 6/03* (2006.01)
*G06T 7/00* (2017.01)
*G06T 7/62* (2017.01)

(52) U.S. Cl.
CPC .............. *A61B 6/504* (2013.01); *A61B 6/032* (2013.01); *A61B 6/469* (2013.01); *A61B 6/5217* (2013.01); *A61B 6/582* (2013.01); *G06T 7/0016* (2013.01); *G06T 7/62* (2017.01); *G06T 2207/10081* (2013.01); *G06T 2207/20224* (2013.01); *G06T 2207/30101* (2013.01)

(58) Field of Classification Search
CPC ....... A61B 6/504; A61B 6/5217; A61B 6/582; G06T 2207/30101
See application file for complete search history.

(56) References Cited

U.S. PATENT DOCUMENTS

| | | | |
|---|---|---|---|
| 4,692,864 A | * | 9/1987 | Shimoni ............... A61B 6/481 348/E5.089 |
| 2004/0171932 A1 | * | 9/2004 | Raman ............... A61B 5/02007 600/425 |

OTHER PUBLICATIONS

Molloi et al., Accurate quantification of vessel cross-sectional area using CT angiography: a simulation study, Int J Cardiovasc Imaging (2017) 33:411-419.

* cited by examiner

*Primary Examiner* — Rajeev P Siripurapu
(74) *Attorney, Agent, or Firm* — Shimokaji IP

(57) ABSTRACT

A method of measuring vessel cross-sectional area includes imaging the cross-sectional area of the vessel, wherein the imaging includes: a central calibration region of interest (ROI) of the vessel to obtain a true Hounsfield unit (HU); an object ROI that includes a vessel area affected by a partial volume effect to obtain an object HU; a ring ROI that is outside the object ROI to obtain a background HU; and integrating the true HU, the object HU, and the background HU to calculate the cross-sectional area.

14 Claims, 12 Drawing Sheets

|  | Reader A | Reader B | Integrated HU |
|---|---|---|---|
| Slope | 0.99 | 0.86 | 1.00 |
| Intercept (mm$^2$) | 0.11 | 0.06 | 0.07 |
| Pearson's r | 0.99 | 0.99 | 1.00 |
| RMSD (mm$^2$) | 0.14 | 0.19 | 0.07 |
| RMSE (mm$^2$) | 0.15 | 0.47 | 0.06 |

Figure 12

|  | Reader A | Reader B | Integrated HU | Integrated HU with calcification |
|---|---|---|---|---|
| Slope | 0.94 | 0.98 | 1.02 | 0.99 |
| Intercept (mm$^2$) | 0.17 | -0.26 | -0.09 | 0.18 |
| Pearson's r | 0.99 | 0.99 | 1.00 | 0.99 |
| RMSD (mm$^2$) | 0.32 | 0.34 | 0.09 | 0.44 |
| RMSE (mm$^2$) | 0.35 | 0.51 | 0.10 | 0.41 |

VESSEL CROSS-SECTIONAL AREA MEASUREMENT USING CT ANGIOGRAPHY

BACKGROUND OF THE INVENTION

The present invention generally relates to vessel cross-sectional area and, more particularly, to apparatus and methods to measure vessel cross-sectional area for stenotic vessels.

Accurate measurement of vessel cross-sectional area (CSA) is limited by low spatial resolution and the partial volume effect. Existing techniques for CSA measurement are particularly limited for vessels with small CSAs, which includes the stenotic region. Partial volume effect limits the accurate visualization and measurement of stenosis severity.

Current methods for measuring vessel morphometry do not correctly account for the partial volume effect caused by the limited spatial resolution of the imaging system. Hence, in standard clinical CT images, the measurement becomes unreliable for small vessels as well as highly stenotic vessels. The standard single threshold technique will fail in this case since the required threshold is dependent on the size of the vessel (FIG. 1).

Coronary computed tomography (CT) angiography is a noninvasive method for visualizing coronary atherosclerosis. Over the past decade, coronary CT angiography image quality has progressively improved. However, previous CT angiography studies have observed an overestimation of stenosis severity. Previous reports indicate that CT angiography inaccurately identifies coronary lesions as severe and the identified lesions are the actual cause of ischemia less than one-half of the time. This finding has led to concerns that widespread application of CT angiography may result in unnecessary invasive coronary angiography.

There have been previous efforts to improve the visualization of a stenotic vessel by displaying the images with a standard window and level. Semi-automated techniques include segmenting vessel lumen from the surrounding tissue by setting a threshold Hounsfield unit (HU). However, the threshold is highly dependent on the vessel size so the stenosis severity can be underestimated or overestimated depending on the threshold HU.

Another major limitation of coronary CT angiography is the presence of arterial calcification, which hampers visualization and measurement of stenosis severity. There have been previous efforts to measure CSA in the presence of calcification by subtracting a pre-contrast image to eliminate the calcium signal. However, accuracy of the subtraction technique is highly limited by motion artifacts that are difficult to correct.

Accordingly, there is a need for apparatus and methods to accurately measure lumen CSA in the presence of stenosis and/or calcification.

SUMMARY OF THE INVENTION

In one aspect of the present invention, a method of measuring vessel cross-sectional area comprises imaging the cross-sectional area of the vessel, wherein the imaging includes: a central calibration region of interest (ROI) of the vessel to obtain a true Hounsfield unit (HU); an object ROI that includes a vessel area affected by a partial volume effect to obtain an object HU; a ring ROI that is outside the object ROI to obtain a background HU; and integrating the true HU, the object HU, and the background HU to calculate the cross-sectional area.

In another aspect of the present invention, a method of measuring vessel cross-sectional area comprises determining a mean Hounsfield unit (HU) inside of the vessel while excluding a partial volume effect; determining a mean HU outside of the vessel; and integrating the mean inside HU and mean outside HU to calculate the cross-sectional area.

In a further aspect of the present invention, a method of measuring vessel cross-sectional area in the presence of calcification comprises obtaining a pre-contrast image of the cross-sectional area; determining a mean Hounsfield unit (HU) inside of the vessel while excluding a partial volume effect; determining a mean HU outside of the vessel; integrating the mean inside HU and mean outside HU to obtain an integrated HU; and subtracting the pre-contrast image from the integrated HU to calculate the cross-sectional area accounting for calcification.

In yet another aspect of the present invention, a system for measuring vessel cross-sectional area comprises a CT scanner configured to image: a central calibration region of interest (ROI) of the vessel to obtain a true Hounsfield unit (HU); an object ROI that includes a vessel area affected by a partial volume effect to obtain an object HU; a ring ROI that is outside the object ROI to obtain a background HU; a processor in communication with the CT scanner, wherein the processor is configured to: integrate the true HU, the object HU, and the background HU to calculate the cross-sectional area.

In an additional aspect of the present invention, a system for measuring vessel cross-sectional area comprises a CT scanner configured to image an inside of the vessel; a processor in communication with the CT scanner, wherein the processor is configured to: obtain a mean Hounsfield unit (HU) inside of the vessel while excluding a partial volume effect; obtain a mean HU outside of the vessel; and integrate the mean inside HU and mean outside HU to calculate the cross-sectional area.

In an additional aspect of the present invention, a system for measuring vessel cross-sectional area comprises a CT scanner configured to: obtain a pre-contrast image inside of the vessel; obtain a post-contrast image inside of the vessel; a processor in communication with the CT scanner, wherein the processor is configured to: obtain a mean Hounsfield unit (HU) inside of the vessel while excluding a partial volume effect; obtain a mean HU outside of the vessel; integrate the mean inside HU and mean outside HU to obtain an integrated HU; and subtract the pre-contrast image from the integrated HU to calculate the cross-sectional area accounting for calcification.

These and other features, aspects and advantages of the present invention will become better understood with reference to the following drawings, description and claims.

BRIEF DESCRIPTION OF THE DRAWINGS

FIG. 11 is a table of linear regression analysis for readers and the integrated HU technique—without stenosis.

FIG. 12 is a table of linear regression analysis for readers and the integrated HU technique—with stenosis.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, the present invention provides apparatus and methods to determine the CSA of vessels in coronary CT angiography by measuring the integrated HU, correctly accounting for the partial volume effect and the presence of calcification. The present invention does not depend on the spatial resolution of an imaging system since the integrated HU is used for a CSA measurement rather than a vessel dimension. The present invention is capable of quantifying a small CSA despite the partial volume effect.

According to the present invention, an integrated HU based approach for CSA measurement is used, with a premise that although the HU of a certain voxel is influenced by the partial volume effect, the total integrated HU within a region of interest (ROI) is conserved. This premise is valid due to the fact that the signal from the iodinated contrast is shared between different voxels but the total signal does not change.

Figure 1:
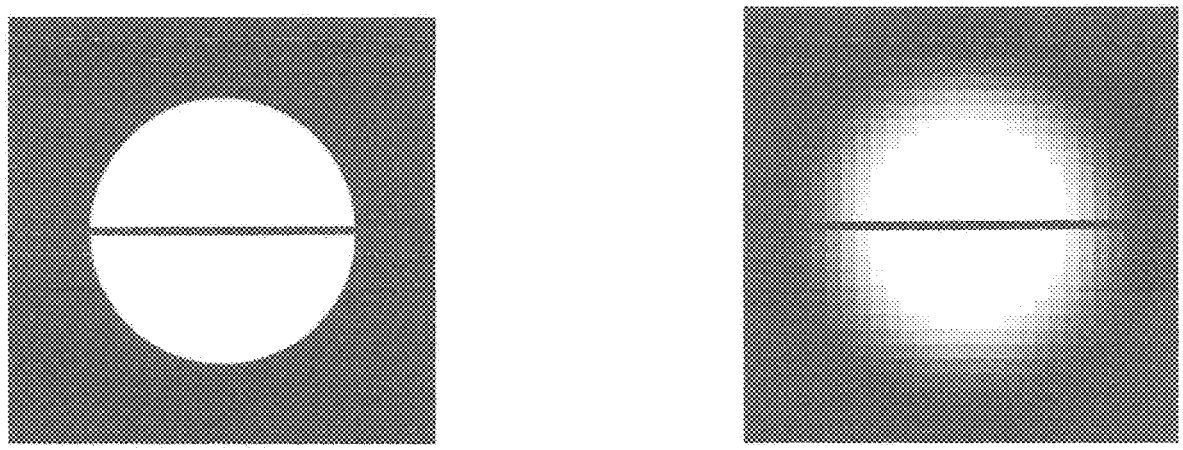
FIG. 1 are images and profiles of vessels with (a) and without (b) the partial volume effect. A standard thresholding level at 150 HU is also shown.
Figure 1:
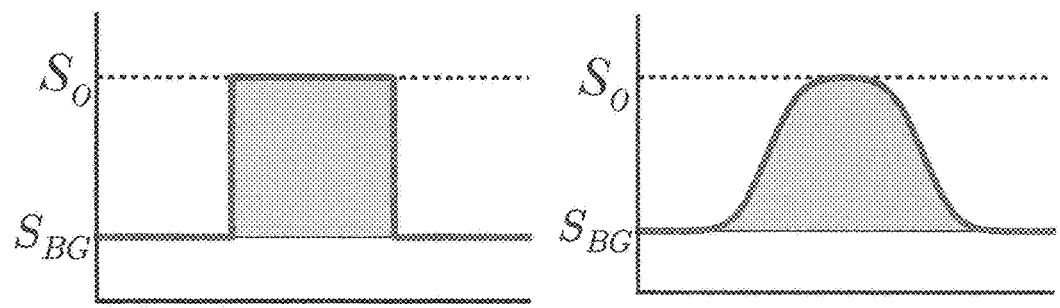
Figure 1:
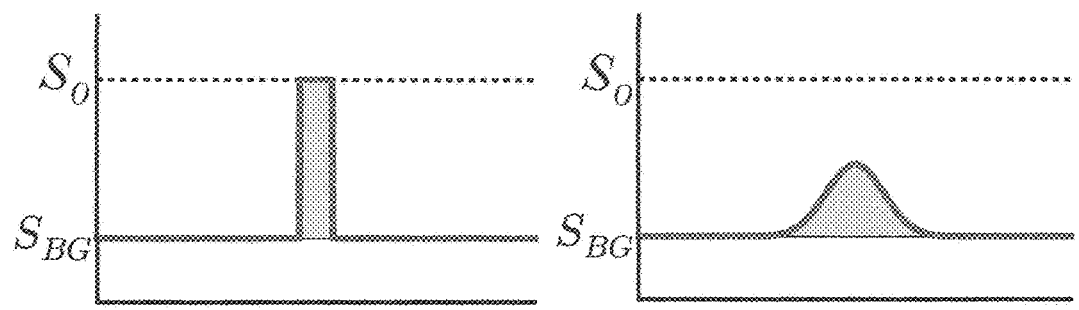
Figure 2:
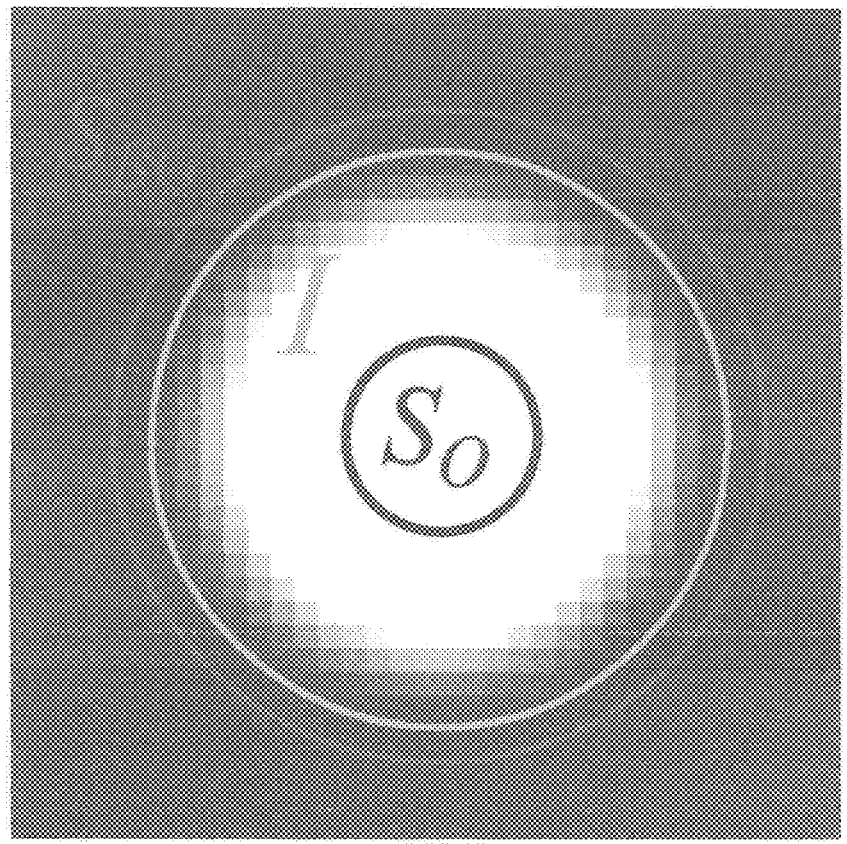
FIG. 2 is an image that shows a simulated vessel lumen with ROIs for CSA measurement where the central ROI that yields $S_O$ and the background ROI that yields $S_{BG}$ are unaffected by partial volume effect while the object ROI used to calculate I is affected by partial volume effect, according to an embodiment of the present invention.

A generalized concept behind the present invention is shown in FIG. 2, which depicts a simple model of a vessel with two materials: high HU iodine solution within the vessel lumen and relatively low HU of epicardial fat (modeled as lipid) surrounding the vessel. There are three ROIs: (1) a central calibration ROI which includes only pixels that are unaffected by the partial volume effect to measure the true HU in the lumen ($S_O$), (2) an object ROI which includes the entire iodine signal in the lumen, including any pixels that are affected by the partial volume effect, and (3) a ring ROI just outside the object ROI to measure the background HU ($S_{BG}$). The integrated HU (I) measured from the object ROI includes the partial volume effect. However, using the above premise about signal conservation, it is the same as the integrated signal without the partial volume effect and can be written as:

$$I = (A - CSA) \times S_{BG} + CSA \times S_O \quad (1)$$

where A is the total area of object ROI. Hence, CSA can be derived as:

$$CSA = \frac{I - A \times S_{BG}}{S_O - S_{BG}} \quad (2)$$

EXAMPLES

Simulation

Polyenergetic fan beam CT simulations were performed using software written in MATLAB. The x-ray spectrum was generated with a spectral model using interpolating polynomials employing the TASMIP algorithm. Phantoms were defined by a collection of ellipses of different materials. The forward projections were computed analytically. The energy dependent linear attenuation coefficients for the materials in the simulated phantoms were generated based on their chemical composition. Quantum noise was simulated with Poisson statistics. Poisson statistics were used to simulate the noise in the sinogram for each pixel, based on the simulated photon counts that it received. Thus, the quantum noise level in an open field was proportional to the square root of the exposure used in the simulation. The analytical model for simulating the forward projections did not include Compton scatter. However, the exclusion of Compton scatter is not expected to affect the inventive method for CSA measurement, as a fundamental theory of the inventive method will remain the same with or without Compton scatter. The detector has a pixel pitch of 0.5 mm and was assumed to have an energy response function that is proportional to the incident photon energy. Gaussian blurring along the detector line was applied to the projected images to simulate the effect of focal spot blurring. Simulation parameters were selected to match the geometry of a 320-slice CT scanner (Aquilion One, Toshiba American Medical Systems, Tustin, Calif.). The simulated images were matched to the experimental images, in terms of CT number, noise, spatial resolution, and contrast to noise ratio (CNR). A standard ramp filter was used for reconstruction, but simulation parameters were adjusted in order to produce a reconstructed CT image that was similar to the clinical CT scanner. All images were simulated at 100 kVp with an equivalent $CTDI_{vol}$ of 7.6 mGy. Images were reconstructed using a slice thickness of 0.5 mm with a MATLAB-based image reconstruction toolkit using filtered back projection but the technique is also expected to work with the existing iterative reconstruction algorithms. The pixel size in the reconstructed slices was selected to be approximately 0.1 mm to improve visualization and allow for more precise ROI selection.

Figure 3:
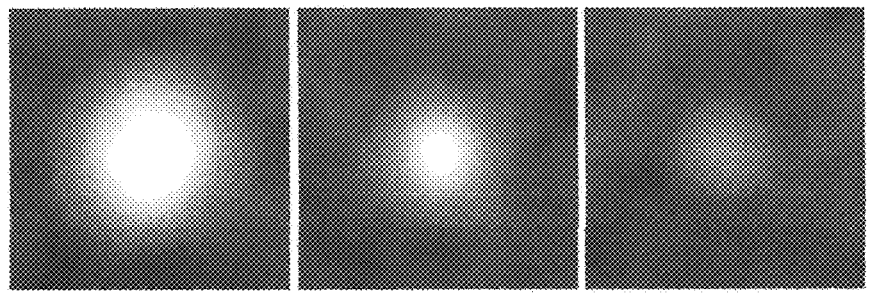
FIG. 3 are images with (a) and without (b) stenosis along with an image with (c) calcification.
Figure 3:
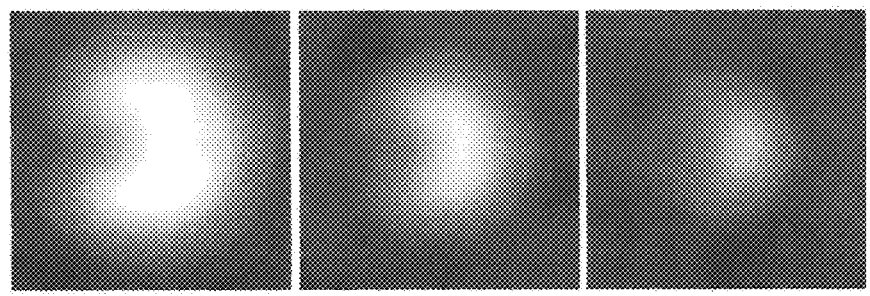
Figure 3:
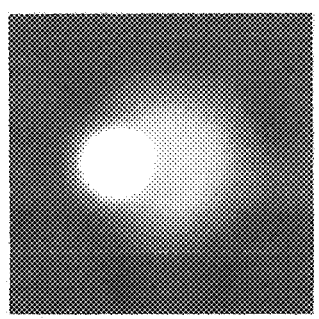

In simulation, a two material model local to coronary vasculature was assumed. Contrast enhanced lumen was modeled as an 8 mg/ml iodine solution and background as lipid. The average and standard deviation were 288±16 HU and −142±17 HU for iodine solution and lipid, respectively. Normal vessels were simulated by circles whose diameters range from 0.1-3 mm in steps of 0.2 mm. To simulate lesions, 2 mm, 3 mm, and 4 mm diameter vessels were simulated with area stenoses from 10% to 90% in steps of 10%. The occlusion was created by a circular region of lipid placed within the lumen resulting in a crescent shaped lumen. Each vessel was simulated three times to obtain multiple noise realizations for a total of 126 vessels. FIG. 3 shows example images of vessels with and without stenosis.

The CSA method of the present invention can also be applied when there are additional materials near the vessel. We evaluated its performance in the presence of a calcification using pre- and post-contrast images for correction of the calcification signal. Calcification was represented as a 0.3 mm$^2$ stenosis with a signal of 1100 HU embedded in vessels in a diameter range of 2-4 mm. Simulated images were generated for vessels filled with both blood and iodinated contrast. The integrated density in the object ROI from the pre-contrast image was subtracted from the integrated density of the post-contrast image to remove the calcium and background signal from the measurement. In the simulation, there was perfect registration between the scans, but some mis-registration can be expected in clinical images. Therefore, to simulate slight mis-registration, measurements were repeated with the vessels in the pre-contrast image shifted by 0.35 mm.

Reader Assessment of CSA

All analysis was completed on a dedicated workstation with custom graphical user interface (GUI) software written in MATLAB. Vessels were presented in a random order with the constraint that realizations of the same vessel were separated by at least three images. The vessel was displayed at the center of a square viewing window 8 mm on each side. Two trained readers performed CSA measurements in simulated vessels with and without stenosis using hand-delineated ROIs with the GUI software. Following a previous report, the display window and level were set automatically at 155% and 65% of the mean luminal enhancement, respectively. However, readers were allowed to freely adjust the display settings for better visualization, especially for small vessels where the partial volume effect greatly reduced the lumen HU.

The object ROIs for the integrated HU technique were first automatically generated based on the known radius of the vessels, and then adjusted manually to ensure the inclusion of the entire lumen with iodinated blood. Once the object ROIs were determined, the ring ROIs were automatically drawn concentrically using a radius that was 1.2 times higher than that of the object ROIs. One calibration ROI was made at the center of a large vessel to measure the true iodine signal without the partial volume effect. The mean pixel values and areas of these three ROIs were recorded automatically and used for CSA calculation using Eq. 2.

Statistical Analyses

The root-mean-square (RMS) deviations from the fit and the RMS errors to the known values were calculated to assess the precision and accuracy, respectively, of the measurement. Reliability of the CSA measurements was evaluated using the coefficient of variation (CV). The coefficient of variation is computed from the independent realizations of each vessel by taking the ratio of the standard deviation over the mean.

Results

Figure 4:
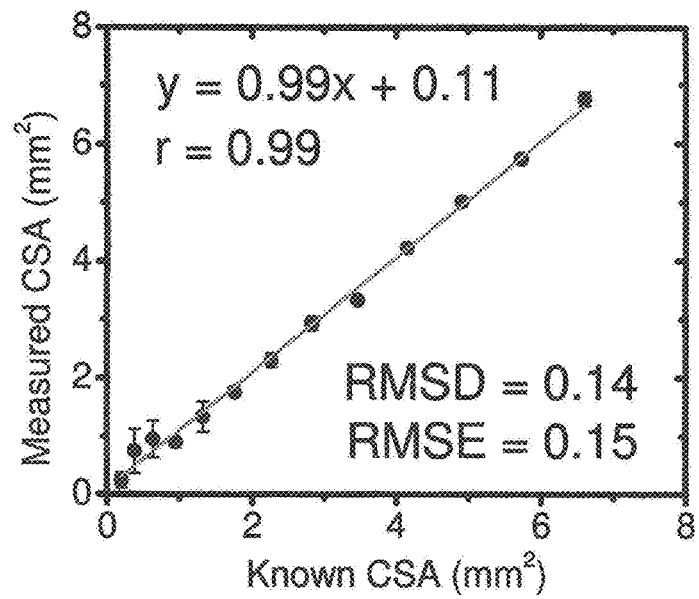
FIG. 4 are graphs of linear regression analysis comparing measured CSA by two readers, (a) and (b), to the known CSA for vessels without stenosis. The best fit line, its equation and Pearson's r value are shown in each plot.
Figure 4:
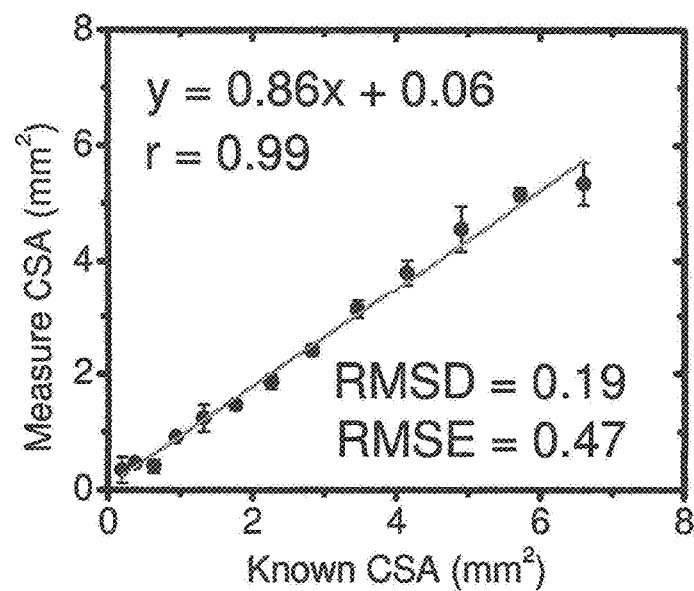
Figure 5:
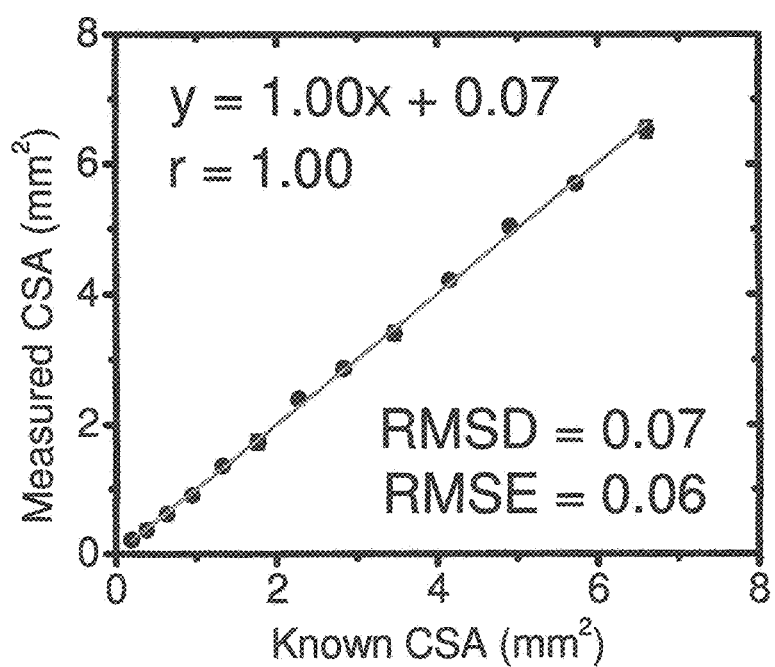
FIG. 5 is a graph of linear regression analysis comparing measured CSA using the integrated HU technique to the known CSA for vessels without stenosis, according to an embodiment of the present invention. The best fit line, its equation and Pearson's r value are shown.

FIGS. 4 and 5 show the CSA measurements of the vessels without stenosis performed by two readers and the semi-automated integrated HU technique of the present invention, respectively.

Figure 6:
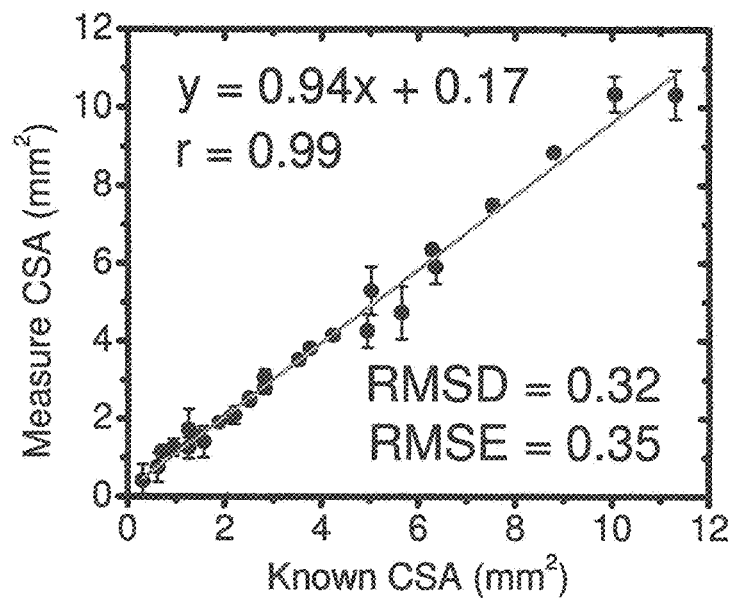
FIG. 6 are graphs of linear regression analysis comparing measured CSA by two readers, (a) and (b), to the known CSA for vessels with stenosis. The best fit line, its equation and Pearson's r value are shown in each plot.
Figure 6:
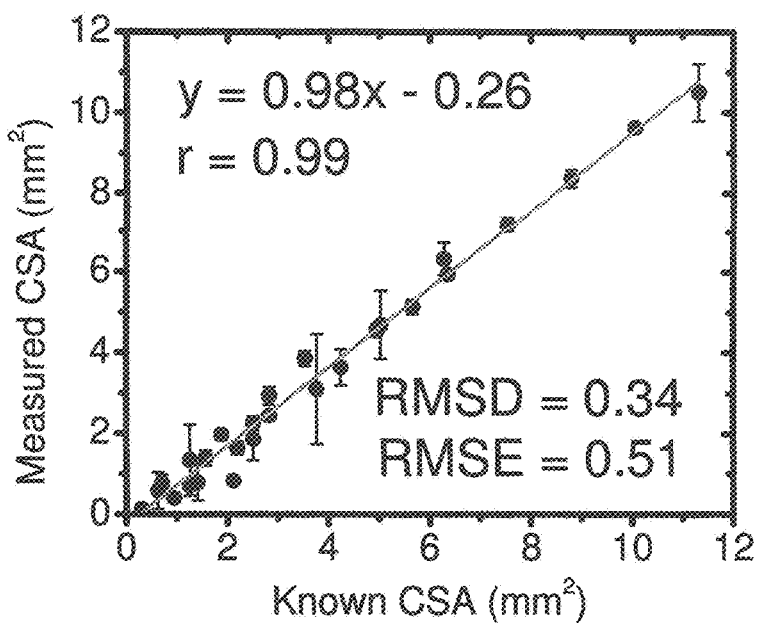
Figure 7:
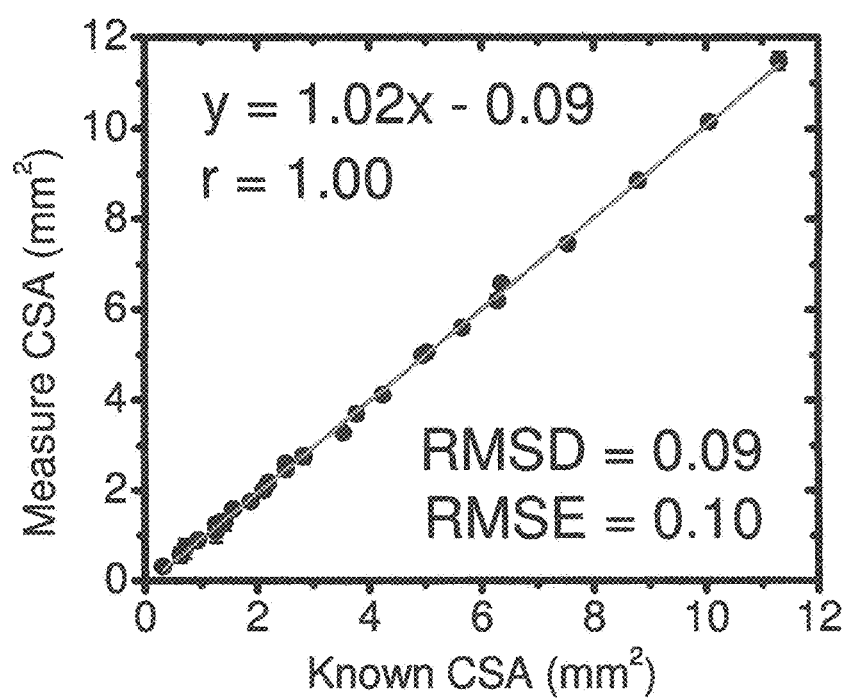
FIG. 7 is a graph of linear regression analysis comparing measured CSA using the integrated HU technique to the known CSA for vessels with stenosis, according to an embodiment of the present invention. The best fit line, its equation and Pearson's r value are shown.

FIGS. 6 and 7 show the CSA measurements of the vessels with stenosis performed by two readers and the semi-automated integrated HU technique of the present invention, respectively.

FIGS. 11 and 12 respectively show table summaries of the linear regression analysis for the readers and the integrated HU technique of the present invention in vessels without and with stenosis. The root mean square difference (RMSD) and the root mean square error (RMSE) represent precision and accuracy, respectively.

Figure 8:
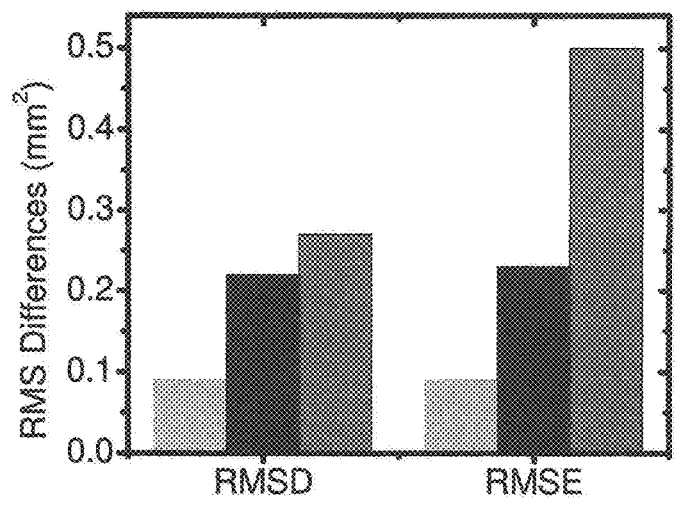
FIG. 8 are graphs of comparisons of precision and accuracy quantified by the root-mean-square deviations from the best fit line (RMSD), and the root-mean-square errors to the known values (RMSE), respectively. The integrated HU technique (green) shows a factor of two improvement for (a) vessels without stenosis and about a factor of three improvement for (b) the vessels with stenosis as compared with the two readers (black and blue).
Figure 8:
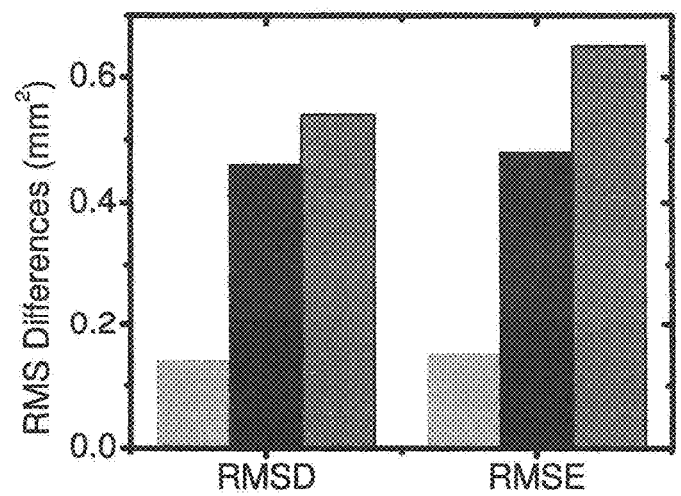

FIG. 8 shows a comparison of precision (RMS deviation) and accuracy (RMS error) for vessels with and without stenosis. Although a good correlation was found in the manual method, the overall RMS error was approximately twice as large as the result from the integrated HU technique of the present invention for vessels without stenosis and three times as large for vessels with stenosis.

Figure 9:
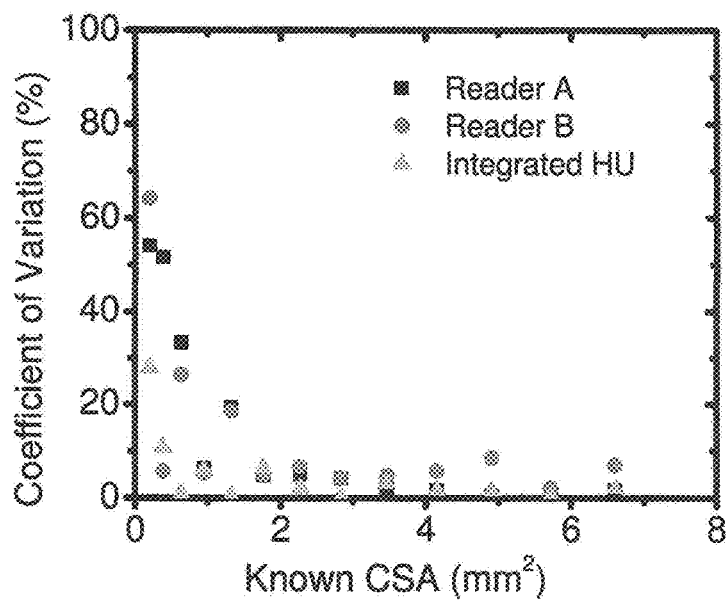
FIG. 9 are graphs of reliability of the CSA measurements for the readers and for the integrated HU technique using the coefficient of variation. The coefficient of variation is computed from the independent realizations of each vessel by taking the ratio of the standard deviation over the mean.
Figure 9:
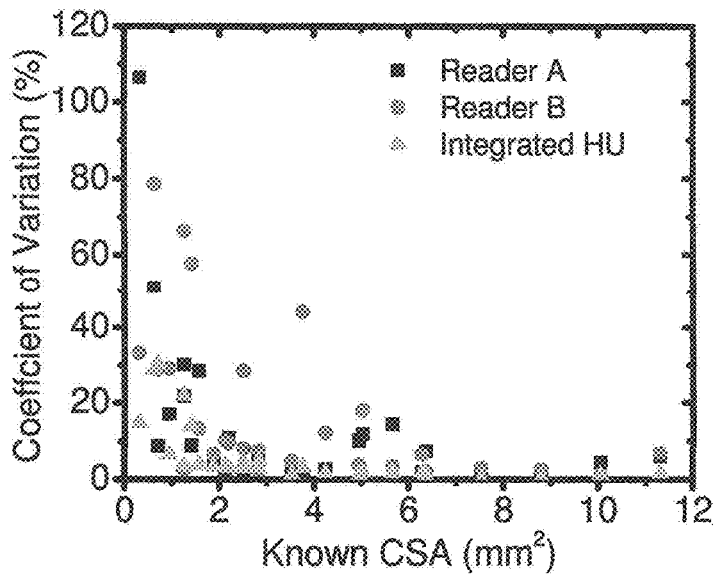

FIG. 9 shows the coefficient of variation for the integration method of the present invention and the two readers in the vessels (a) without and (b) with stenosis. The errors for the readers were higher for vessels with smaller CSA, where the measurement was limited due to the partial volume effect. This is particularly true for vessels with CSA less than 4 mm$^2$, where significant scatter can be seen from the manual method. Moreover, for CSA less than 1 mm$^2$, both readers had difficulty detecting the lumen, while the integration technique of the present invention was still able to predict the CSA with relatively good accuracy.

Figure 10:
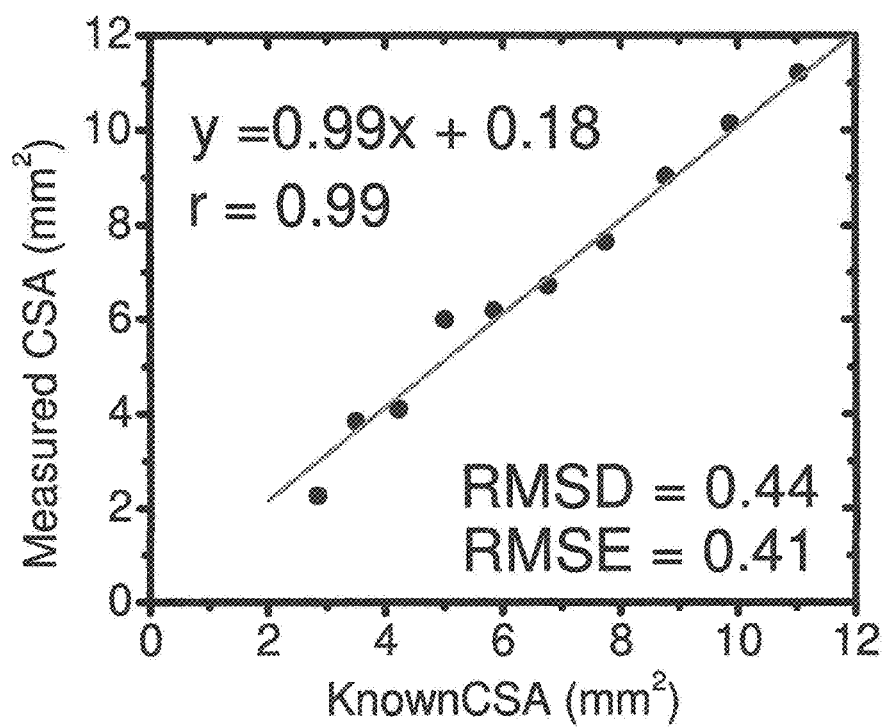
FIG. 10 is a graph of correlation between measured and known CSA with calcification. The best fit line, its equation and Pearson's r value are shown.
Figure 13:
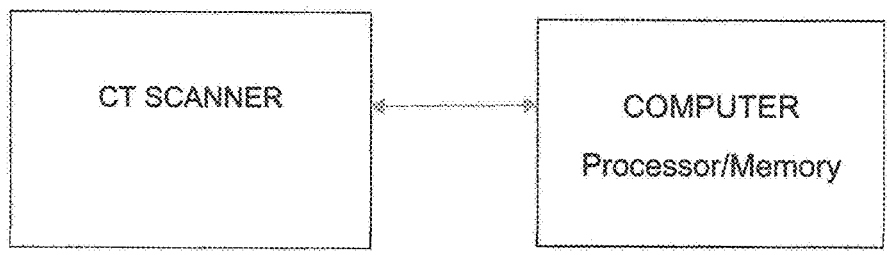
FIG. 13 is an exemplary system according to an embodiment of the present invention.

The effect of calcium on CSA measurement in the case of arterial calcification can be reduced by subtracting the integrated HU from a registered pre-contrast image. FIG. 10 shows the CSA measurement results after correction for calcium signal. The measured CSA is in good agreement with the known CSA. To simulate slight mis-registration, measurements were repeated with the vessels in the pre-contrast image shifted by 0.35 mm. The maximum change in the measured CSA was 0.08 mm$^2$ with an average change of 0.014 mm$^2$, which is much smaller than the RMS error of 0.41 mm$^2$.

Summary

Coronary CT angiography is currently limited by the partial volume effect. The present invention provides, in embodiments, an automated technique that can accurately measure lumen CSA in the presence of stenosis by accounting for the partial volume effect. Our simulation results show that the integrated HU can be used to accurately measure vessel CSA by accounting for the partial volume effect. The results of our semi-automatic technique show that it can improve the precision and accuracy of vessel CSA as compared with the existing manual technique. The semi-automated integrated HU technique showed a factor of two improvement in precision and accuracy for vessels without stenosis and approximately a factor of three improvement for vessels with stenosis. This is particularly true in the case of small vessel diameters where the CSA measurement is more limited by partial volume effect. The measured coefficient of variation for CSA measurements using the integrated HU technique of the present invention in vessels without stenosis was less than 10% for lumen areas greater than 2 mm² while for the manual technique this lumen area was more than 6 mm². This shows a substantial reduction in variability of CSA measurement for small vessel diameters using the semi-automated integrated HU technique of the present invention.

In embodiments, the integrated HU technique of the present invention includes a determination of the mean HU inside and outside the vessel lumen, which is unaffected by partial volume effect for accurate measurement of vessel CSA. This can be accomplished by measuring the mean HU at the center of the lumen and far enough away from the vessel wall so that it will not be affected by the partial volume effect. However, in the case of a stenosis, the HU inside the lumen can be entirely affected by partial volume effect. Therefore, in the case of a stenosis, the unaffected HU can be estimated by averaging the HU in the normal lumen before and after the stenosis.

Coronary artery calcification is another major limitation for accurate measurement of CSA. Our invention is based on integrated HU and it is immune to motion mis-registration as long as the calcified region stays within the object ROI for the pre- and post-contrast images. The results show that the integrated HU technique in conjunction with a registered pre-contrast image can be used to accurately measure lumen area even in the presence of calcification. The subtraction technique has previously been investigated and it works well when there is good registration between the two scans, but some mis-registration can be expected. To simulate slight mis-registration, measurements were repeated with the vessels in the pre- and post-contrast image shifted from each other. Our results show that the measured error in the integrated HU was relatively small with the expected motion mis-registration. The use of integrated HU makes the method more robust against registration errors due to the averaging of many pixels.

CT angiography image data has recently been used to derive fractional flow reserve (FFR) to estimate the physiological severity of a stenosis. In this approach, the geometrical parameters of the stenosis and arterial tree are used to perform computational fluid dynamics and estimate pressure drop across the stenosis. A previous report has shown that lesion CSA and flow rate are the most important parameters for accurate estimation of FFR based on stenosis geometrical parameters. Therefore, accurate measurement of lesion CSA is expected to also improve existing techniques for estimation of FFR based on CT angiography image data.

The integrated HU technique, in embodiments, uses the mean HU inside and outside the lumen for measurement of CSA, both of which were estimated using a large region of interest inside and a ring region of interest outside the lumen to minimize any potential error in CSA estimation. However, large variation in HU close to vessel lumen, such as calcification, can potentially introduce error in CSA estimation. Therefore, lumen CSA measurement in the presence of calcification requires a registered pre-contrast image, which can be used to subtract the integrated HU due to the calcification. This indicates that a large motion mis-registration with the pre-contrast image can potentially introduce error in CSA measurement.

As can be seen, the present invention uses, in embodiments, a semi-automated integrated Hounsfield unit technique that yields more than a factor of two improvement in accuracy as compared to the existing manual technique for vessels with and without stenosis. This technique can also be used to correct for the effect of coronary calcification.

As will be appreciated by one skilled in the art, the present invention may be embodied as a system, a method or a computer program product. Accordingly, the present invention may take the form of an entirely hardware embodiment, an entirely software embodiment (including firmware, resident software, micro-code, etc.) or an embodiment combining software and hardware aspects. Furthermore, the present invention may take the form of a computer program product embodied in any tangible medium of expression having computer usable program code embodied in the medium. Any combination of one or more computer usable or computer readable medium(s) may be utilized.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CDROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

It should be understood, of course, that the foregoing relates to exemplary embodiments of the invention and that modifications may be made without departing from the spirit and scope of the invention as set forth in the following claims.

I claim:

1. A method of diagnosing stenosis in a blood vessel, comprising:
   imaging, via a CT scanner, a cross-section of the vessel and a background area surrounding the vessel cross section, wherein the imaging is of:
   a central region of interest (ROI), which is inside the vessel cross section, to measure the central ROI in terms of a true Hounsfield unit (HU) ($S_O$);
   an object ROI, which is inside the vessel cross section and includes the central ROI and is affected by a partial volume effect, to measure the object ROI in terms of an object HU (I);
   a ring ROI, which is in the background area, to measure the ring ROI in terms of a background HU ($S_{BG}$);
   using, via a processor, the true HU, the object HU, and the background HU to calculate a cross-sectional area (CSA) of the vessel cross section;

wherein the calculated cross-sectional area (CSA) is defined by:

$$CSA = \frac{I - A \times S_{BG}}{S_O - S_{BG}}$$

where A=total area of the object ROI; and
using, via the processor, the calculated cross-sectional area to minimize underestimation and overestimation of severity of stenosis in the vessel.

2. The method of claim 1, wherein the vessel has calcification.

3. The method of claim 1, wherein the ring ROI has a radius that is 1.2 times larger than a radius of the object ROI.

4. A method of diagnosing stenosis in a blood vessel, comprising:
measuring, via an imaging of a cross section of the vessel, a central region of interest (ROI) which is in the vessel cross section, to obtain a mean true Hounsfield unit (HU) ($S_O$);
measuring, via the imagining of the cross section of the vessel, an object ROI which is in the vessel cross section and includes the central ROI and is affected by a partial volume effect, to obtain a mean object HU (I) that includes a partial volume effect of the vessel cross section;
measuring, via an imaging of a background area outside of the vessel cross section, the background area to obtain a mean background HU ($S_{BG}$);
using, via a processor, the mean true HU, the mean object HU, and the mean background HU to calculate a cross-sectional area of the vessel cross section;
wherein the calculated cross-sectional area (CSA) is defined by:

$$CSA = \frac{I - A \times S_{BG}}{S_O - S_{BG}}$$

where A=total area of the object ROI; and
using, via the processor, the calculated cross-sectional area to minimize underestimation and overestimation of severity of stenosis in the vessel.

5. The method of claim 4, wherein measuring the central ROI includes measuring the central ROI at only a center of the vessel.

6. The method of claim 5, wherein measuring the central ROI includes measuring the central ROI radially inward from a vessel wall to exclude the partial volume effect.

7. The method of claim 5, wherein:
the method further comprises obtaining the mean object HU before stenosis and the mean object HU with stenosis.

8. A method of diagnosing stenosis in a blood vessel having calcification, comprising:
measuring, via a pre-contrast imaging of a cross section of the vessel, an object ROI which is inside the vessel cross section and is affected by a partial volume effect, to obtain a pre-contrast mean object HU that includes a partial volume effect of the vessel cross section;
measuring, via a post-contrast imaging of the cross section of the vessel, a central ROI which is inside the object ROI, to obtain a post-contrast mean true HU ($S_O$);

measuring, via the post-contrast imagining of the cross section of the vessel, the object ROI, to obtain a post-contrast mean object HU that includes the partial volume effect of the vessel cross section;
measuring, via a post-contrast imaging of a background area outside of the vessel cross section, the background area in terms of a post-contrast mean background HU ($S_{BG}$);
using the post-contrast mean true HU, the pre-contrast mean object HU, the post-contrast mean object HU, and the post-contrast mean background HU to obtain an integrated HU that is representative of a calculated cross-sectional area (CSA) of the vessel cross section;
wherein the calculated CSA is defined by:

$$CSA = \frac{I - A \times S_{BG}}{S_O - S_{BG}}$$

where A=total area of the object ROI and where I=subtracting the pre-contrast mean object HU from the post-contrast mean object HU, accounting for the calcification; and
using the calculated cross-sectional area to minimize underestimation and overestimation of severity of stenosis in the vessel.

9. The method of claim 8, wherein measuring the central ROI, via post-contrast imaging, includes measuring the central ROI at only a center of the vessel.

10. The method of claim 8, wherein measuring the central ROI, via post-contrast imaging, includes measuring the central ROI radially inward from a vessel wall to exclude the partial volume effect.

11. A system for diagnosing stenosis in a blood vessel, comprising:
a CT scanner that images:
a central region of interest (ROI), which is inside a cross section of the vessel, to measure the central ROI in terms of a true Hounsfield unit (HU) ($S_O$);
an object ROI, which is inside the vessel cross section and includes the central ROI and is affected by a partial volume effect, to measure the object ROI in terms of an object HU (I);
a ring ROI, which is in a background area that is outside of the vessel cross section, to measure the ring ROI in terms of a background HU ($S_{BG}$);
a processor in communication with the CT scanner, wherein the processor:
uses the true HU, the object HU, and the background HU to calculate a cross-sectional area (CSA) of the vessel cross section;
wherein the calculated cross-sectional area (CSA) is defined by:

$$CSA = \frac{I - A \times S_{BG}}{S_O - S_{BG}}$$

where A=total area of the object ROI; and
uses the calculated cross-sectional area to minimize underestimation and overestimation of severity of stenosis in the vessel.

12. A system for diagnosing stenosis in a blood vessel, comprising:
a CT scanner that images an area inside of the vessel and an area outside of the vessel;

a processor in communication with the CT scanner, wherein the processor:
obtains a measured mean true Hounsfield unit (HU) ($S_O$) from the image of the area inside of the vessel while excluding a partial volume effect inside of the vessel;
obtains a measured mean object HU (I) from the image of the area inside of the vessel while including the partial volume effect inside of the vessel;
obtains a measured mean background HU ($S_{BG}$) from the image of the area outside of the vessel; and
uses the mean true HU, the mean object HU, and the mean background HU to calculate a cross-sectional area of the inside of the vessel;
wherein the calculated cross-sectional area (CSA) is defined by:

$$CSA = \frac{I - A \times S_{BG}}{S_O - S_{BG}}$$

where A=total area of the object ROI; and
uses the calculated cross-sectional area to minimize underestimation and overestimation of severity of stenosis in the vessel.

13. A system for diagnosing stenosis in a blood vessel in the presence of calcification, comprising:
a CT scanner that:
provides a pre-contrast image of an area inside of the vessel;
provides a post-contrast image of the area inside of the vessel;
provides a post-contrast image of an area outside of the vessel;
a processor in communication with the CT scanner, wherein the processor:
obtains a pre-contrast mean object Hounsfield unit (HU) that is measured from the pre-contrast image that includes an object region of interest (ROI) which has a partial volume effect;
obtains a post-contrast mean true HU that is measured from the post-contrast image of a central ROI which is part of the area inside of the vessel and does not have the partial volume effect;
obtains a post-contrast mean object HU that is measured from the post-contrast image that includes the object ROI which has the partial volume effect;
obtains a post-contrast mean background HU that is measured from the post-contrast image of the area outside of the vessel;
uses the post-contrast mean true HU, the pre-contrast mean object HU, the post-contrast mean object HU, and the post-contrast mean background HU to obtain an integrated HU that is representative of a calculated cross-sectional area (CSA) of the vessel cross section;
wherein the calculated CSA is defined by:

$$CSA = \frac{I - A \times S_{BG}}{S_O - S_{BG}}$$

where A=total area of the object ROI and I=subtracting the pre-contrast mean object HU from the post-contrast mean object HU, accounting for the calcification; and
uses the calculated cross-sectional area to minimize underestimation and overestimation of severity of stenosis in the vessel.

14. A non-transitory computer readable medium with computer executable instructions stored thereon, executed by a processor, to perform a method of diagnosing stenosis in a blood vessel, the method comprising:
imaging, via a CT scanner, a cross-section of the vessel and a background area surrounding the vessel cross section, wherein the imaging is of:
a central region of interest (ROI), which is inside the vessel cross section, to measure the central ROI in terms of a true Hounsfield unit (HU) ($S_O$);
an object ROI, which is inside the vessel cross section and includes the central ROI and is affected by a partial volume effect, to measure the object ROI in terms of an object HU (I);
a ring ROI, which is in the background area, to measure the ring ROI in terms of a background HU ($S_{BG}$);
using, via a processor, the true HU, the object HU, and the background HU to calculate a cross-sectional area (CSA) of the vessel cross section;
wherein the calculated cross-sectional area (CSA) is defined by:

$$CSA = \frac{I - A \times S_{BG}}{S_O - S_{BG}}$$

where A=total area of the object ROI; and
using, via the processor, the calculated cross-sectional area to minimize underestimation and overestimation of severity of stenosis in the vessel.

* * * * *